(12) United States Patent
Zellerhoff et al.

(10) Patent No.: US 11,717,239 B2
(45) Date of Patent: Aug. 8, 2023

(54) PROVIDING A 3D IMAGE DATASET OF AN EXAMINATION OBJECT

(71) Applicant: Siemens Healthcare GmbH, Erlangen (DE)

(72) Inventors: Michael Zellerhoff, Pretzfeld (DE); Michele Kiessling, Erlangen (DE); Michael Manhart, Fürth (DE); Thomas Brunner, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 173 days.

(21) Appl. No.: 17/390,209

(22) Filed: Jul. 30, 2021

(65) Prior Publication Data

US 2022/0031265 A1    Feb. 3, 2022

(30) Foreign Application Priority Data

Jul. 31, 2020   (DE) .................... 10 2020 209 703.8

(51) Int. Cl.
*A61B 6/00* (2006.01)
*A61B 6/03* (2006.01)

(52) U.S. Cl.
CPC ............ *A61B 6/4028* (2013.01); *A61B 6/032* (2013.01); *A61B 6/466* (2013.01); *A61B 6/5205* (2013.01)

(58) Field of Classification Search
CPC ..... A61B 6/4028; A61B 6/4208; A61B 6/469; A61B 6/466; A61B 6/4441; A61B 6/5211;
(Continued)

(56) References Cited

U.S. PATENT DOCUMENTS

2008/0089467 A1    4/2008 Lauritsch et al.
2008/0089468 A1*   4/2008 Heigl ................... A61B 6/4458
                                                          378/20
(Continued)

FOREIGN PATENT DOCUMENTS

DE   102006037565 B3   2/2008
DE   102006041033 A1   3/2008
(Continued)

OTHER PUBLICATIONS

Defrise, Michel, and Rolf Clack. "A cone-beam reconstruction algorithm using shift-variant filtering and cone-beam backprojection." IEEE transactions on medical imaging 13.1 (1994): 186-195.
(Continued)

*Primary Examiner* — Irakli Kiknadze
(74) *Attorney, Agent, or Firm* — Lempia Summerfield Katz LLC (57) ABSTRACT

First projection images are recorded. The first projection images map an examination object along different first projection directions. A corresponding respective second projection image is recorded for at least two first projection images. The first projection images each have a first focus point, and the second projection images each have a second focus point. Each of the second projection images together with a corresponding first projection image at least partially map a common part of the examination object about a stationary center point. The second projection images map the examination object along second projection directions that are mutually different and at least partially different, relative to the respectively corresponding first projection directions such that a straight line through the first focus point and the second focus point of the mutually corresponding first projection images and second projection images
(Continued)

extends through the stationary center point. The 3D image dataset is reconstructed.

17 Claims, 5 Drawing Sheets

(58) Field of Classification Search
CPC ....... A61B 6/4429; A61B 6/40; A61B 6/4458; A61B 6/032; A61B 6/027; A61B 6/5205; A61B 6/102; A61B 6/487; A61B 6/4464; A61B 6/583; A61B 2090/364; A61B 6/4405; A61B 6/588; A61B 6/4447; A61B 6/022; A61B 6/035; A61B 6/4014; A61B 6/025; A61B 6/4085; A61B 6/4452; A61B 6/03; G01N 23/046; G01N 2223/612; G01N 2223/419; G01N 23/044; G06T 11/006; G06T 2211/421; G06T 2211/432
USPC ............................................. 378/4, 15, 19.62
See application file for complete search history.

(56) References Cited

U.S. PATENT DOCUMENTS

| | | | |
|---|---|---|---|
| 2008/0181367 A1* | 7/2008 | Heigl | A61B 6/4028 378/207 |
| 2008/0304617 A1 | 12/2008 | Brunner et al. | |
| 2009/0135993 A1* | 5/2009 | Harer | A61B 6/589 378/4 |
| 2014/0321612 A1 | 10/2014 | Schäfer et al. | |
| 2015/0371390 A1* | 12/2015 | Gassner | G06T 7/10 382/128 |
| 2016/0220212 A1* | 8/2016 | Duewer | G06T 5/50 |
| 2016/0239632 A1* | 8/2016 | Yu | G16H 50/50 |
| 2016/0306936 A1* | 10/2016 | Mizobe | G16H 30/20 |
| 2017/0032546 A1* | 2/2017 | Westerhoff | G06T 7/0014 |
| 2020/0054297 A1 | 2/2020 | Martinez Ferreira et al. | |
| 2020/0333133 A1* | 10/2020 | Cosneau | G01B 15/045 |

FOREIGN PATENT DOCUMENTS

| | | |
|---|---|---|
| DE | 102007026115 A1 | 12/2008 |
| DE | 102008035657 A1 | 3/2010 |
| DE | 102012208850 A1 | 4/2013 |
| DE | 102010020375 B4 | 6/2016 |

OTHER PUBLICATIONS

German Office Action for German Application No. 10 2020 209 703.8 dated Jun. 18, 2021.

Herbst, Magdalena, et al. "Dynamic detector offsets for field of view extension in C-arm computed tomography with application to weight-bearing imaging." Medical physics 42.5 (2015): 2718-2729.

Nett, Brian E., et al. "Arc based cone-beam reconstruction algorithm using an equal weighting scheme." Journal of X-Ray Science and Technology 15.1 (2007): 19-48.

Noo, Frederic, et al. "Image reconstruction from fan-beam projections on less than a short scan." Physics in medicine & biology 47.14 (2002): 2525-2546.

Noo, Frédéric, et al. "A new scheme for view-dependent data differentiation in fan-beam and cone-beam computed tomography." Physics in Medicine & Biology 52.17 (2007): 5393-5414.

Zambelli, Joseph, et al. "Novel C-arm based cone-beam CT using a source trajectory of two concentric arcs." Medical Imaging 2007: Physics of Medical Imaging. vol. 6510. International Society for Optics and Photonics, 2007. pp. 1-12.

* cited by examiner

PROVIDING A 3D IMAGE DATASET OF AN EXAMINATION OBJECT

This application claims the benefit of German Patent Application No. DE 10 2020 209 703.8, filed on Jul. 31, 2020, which is hereby incorporated by reference in its entirety.

BACKGROUND

The present embodiments relate to a method for providing a three-dimensional (3D) image dataset of an examination object, a medical X-ray device, and a computer program product.

For the 3D imaging of a region of interest of an examination object (e.g., a human and/or animal patient and/or an X-ray phantom), a plurality of projection images is often recorded about a common isocenter using an X-ray device and is subsequently reconstructed. The projection images may be regarded thereby as fluoroscopy images of the examination object. The X-ray device often has an X-ray source for emitting X-rays for irradiating the examination object, and a detector for receiving the X-rays. A significant restriction as compared with a conventional computed tomography (CT) is represented by a limited imaging region due to a size of a detector (e.g., a size of an X-ray sensitive surface of the detector).

Disadvantageously, particular anatomical regions (e.g., a lung and/or a liver of the examination object) cannot be acquired with a single recording of projection images. In addition, due to the limited size of the detector, truncation artifacts often occur (e.g., in the edge regions of the imaging region of the examination object).

SUMMARY AND DESCRIPTION

The scope of the present invention is defined solely by the appended claims and is not affected to any degree by the statements within this summary.

The present embodiments may obviate one or more of the drawbacks or limitations in the related art. For example, a complete 3D imaging of a region of interest of an examination object using a medical X-ray device is enabled.

The present embodiments relate, in a first aspect, to a method for providing a 3D image dataset of an examination object. Therein, in a first act a), a plurality of first projection images of the examination object is recorded. In addition, the plurality of projection images map the examination object along mutually different first projection directions. In a second act (b), a corresponding second projection image of the examination object is recorded for at least two of the first projection images. The first projection images each have a first focus point, and the second projection images each have a second focus point. In addition, each of the second projection images maps, together with the first projection images corresponding thereto, at least partially a common part of the examination object about a stationary center point. Further, the second projection images map the examination object along second projection directions that are mutually different and at least partially different, relative to the respectively corresponding first projection directions such that a straight line through the first focus point and the second focus point of the mutually corresponding first projection images and second projection images extends through the stationary center point. In a third act c), the 3D image dataset is reconstructed from the first projection images and second projection images. Thereafter, in a fourth act d), the 3D image dataset is provided.

In act a), the plurality of first projection images may be recorded by a medical X-ray device (e.g., a medical C-arm X-ray device). Thereby, the medical X-ray device may have an X-ray source and a detector (e.g., an X-ray detector that may be configured as a flat detector). The X-ray source and the detector may be arranged in a defined arrangement (e.g., on a common C-arm), such that the X-ray source and the detector move relative to the examination object. For the recording of the first projection images, the X-ray source may emit X-ray beams that, when the X-ray beams impinge upon a surface of the detector following an interaction with the examination object, may be received by the detector and processed. Therein, the X-ray beams may, for example, have the form of a conical beam and/or a fan beam and/or a parallel beam. In addition, the respective first projection direction for recording the first projection images may correspond to an angulation of the medical X-ray device. Therein, the first projection direction may define a course of a ray (e.g., a central and/or middle ray between the X-ray source and the detector, the detector midpoint) of the medical X-ray device on recording the respective first projection image. In one embodiment, the first projection images may be recorded in temporal sequence (e.g., one after the other).

Further, the first projection images may in each case map the examination object two-dimensionally along one of the first projection directions. In one embodiment, the first projection images may at least partially map a common portion of the examination object along the mutually different projection directions. Therein, the examination object may be, for example, a human and/or animal patient and/or an X-ray phantom.

Further, the portion may denote, for example, a spatial region (e.g., a volume) of the examination object including an anatomical object of interest.

In act (b), a corresponding second projection image of the examination object may be recorded for at least two (e.g., each) of the first projection images. For example, after act b), a plurality of pairs each including a first projection image and a second projection image corresponding to one another may have been recorded. The corresponding second projection images may be recorded, for example, similarly to the first projection images using the medical X-ray device. Therein, the respective second projection direction for recording the second projection images may correspond to an angulation of the medical X-ray device. In addition, the second projection direction may define a course of a ray (e.g., a central and/or middle ray between the X-ray source and the detector, the detector midpoint) of the medical X-ray device on recording the respective second projection image. In one embodiment, the second projection images may be recorded in, particularly direct, temporal sequence to one another and/or in relation to the first projection images. For example, first, the first projection images may be recorded in temporal sequence, where subsequently, the second projection images corresponding thereto may be recorded in temporal sequence.

Further, the first projection images and/or the second projection images may have metadata, where the metadata may include, for example, an item of information regarding a recording parameter and/or an operating parameter of the medical X-ray device.

Further, the second projection images may in each case map the examination object two-dimensionally along one of the second projection directions. Therein, each of the second projection images together with the respectively corresponding first projection image may at least partially map a common portion of the examination object. Further, mutually corresponding first and second projection images may each have first and second projection directions that are at least partially (e.g., completely) different from one another.

The first projection images may each have a first focus point that may define a spatial position of the coming together of the X-rays of the X-ray beam at the time point of the recording of the respective first projection image. Similarly thereto, the second projection images may each have a second focus point that may define a spatial position of the coming together of the X-rays of the X-ray beam at the time point of the recording of the respective second projection image. Alternatively or additionally, the first focus point and/or the second focus point may define a spatial position of the X-ray source (e.g., a panel). For example, the first and/or second focus points may lie in a common plane.

The recording of the first projection images and the second projection images for mapping the at least partially common portion of the examination object may take place about a common stationary center point. Therein, a spatial position of the stationary center point may remain unchanged (e.g., constant during the recording of the first and second projection images). A first isocenter (e.g., a first center of rotation) of the medical X-ray device may be repositioned for recording the first projection images (e.g., between the recording time points of the first projection images). Therein, a spatial distance between the first focus points and the first isocenter may be constant at the time point of the recording of the associated first projection image.

Similarly thereto, a second isocenter (e.g., a second center of rotation) of the medical X-ray device may be repositioned for recording the second projection images (e.g., between the recording time points of the second projection images). The first isocenter and/or the second isocenter may also be positioned at least partially differently from the stationary center point for the recording of the respective projection images. Therein, a spatial distance between the second focus points and the second isocenter may be constant at the respective time point of the recording of the associated at least one second projection image. For example, the spatial distance between the second focus points and the second isocenter, in each case, at the time point of the recording of the associated at least one second projection image may be equal to the spatial distance between the first focus points and the first isocenter at the respective time point of the recording of the associated first projection image. For example, the X-ray source and the detector may each have a constant spatial distance in relation to the first isocenter and/or second isocenter at the time point of the recording of the respective first projection image and/or second projection image.

In addition, the second focus points may be positioned for recording the second projection images such that a straight line through the first focus point and the second focus point of the mutually corresponding first and second projection images extends through the stationary center point. Thus, for each pair of mutually corresponding first and second projection images, there may be a straight line that extends through the stationary center point and through the first focus point and the second focus point belonging to the respective pair. If the first focus point and the second focus point of mutually corresponding first and second projection images have the same spatial position, it may occur that the mutually corresponding first and second projection images have the same or different first and second projection directions. With an identical first and second projection direction, an X-ray dose may be reduced for recording the first and/or second projection image in order to minimize a radiation burden for the examination object.

In one embodiment, the medical X-ray device (e.g., the defined arrangement including the X-ray source and the detector) may be repositioned for recording the first and second X-ray images. Therein, the positioning of the medical X-ray device may include a translation and/or rotation (e.g., an alignment). In one embodiment, the positioning of the medical X-ray device (e.g., the defined arrangement including the X-ray source and the detector) may take place for recording the first and/or second projection images substantially in the common plane. The positioning of the medical X-ray device for recording the first projection images may include, for example, a compound movement, where the first isocenter is moved translationally (e.g., relative to the stationary center point), and the defined arrangement of the X-ray source and the detector about the first isocenter is rotated (e.g., simultaneously with the translation). Similarly thereto, the positioning of the medical X-ray device during the recording of the second projection images may include a compound movement, where the second isocenter is moved translationally (e.g., relative to the stationary center point), and the defined arrangement of the X-ray source and the detector about the second isocenter is rotated (e.g., simultaneously with the translation). The positioning of the medical X-ray device (e.g., the defined arrangement including the X-ray source and the detector for recording the first and second projection images may therein deviate at least partially from a purely rotational movement).

In act c), the 3D image dataset may be reconstructed from the first and second projection images (e.g., iteratively), where the mutually corresponding first and second projection images may be combined in pairs. The reconstruction of the 3D image dataset may take place, for example, by use of a simultaneous algebraic reconstruction technique (SART). For example, the 3D image dataset may have a plurality of image points (e.g., voxels that are arranged along a plurality of planes (e.g., parallel planes) of a recording geometry for recording the first and second projection images.

The provision of the 3D image dataset may include, for example, a storage on a computer-readable storage medium and/or a display on a display unit and/or a transfer to a provision unit. For example, a graphical representation of the 3D image dataset may be displayed on the display unit.

By this, a 3D imaging (e.g., complete 3D imaging) of the portion to be imaged of the examination object in the 3D image data set may be enabled. For example, the portion to be imaged may include a 3D volume that is larger in at least one spatial direction (e.g., in the lateral direction, up to twice as large as in a conventional recording and 3D reconstruction of projection images using a medical X-ray device).

In a further embodiment of the method, the first focus points may form a first path. Therein, the first path may also have at least two successive portions. In addition, the first projection images may be recorded about the first isocenter, which is repositioned for each recording. The positioning of the first isocenter along a movement direction may take place relative to the stationary center point. The movement direction is dependent upon the respective portion of the first path. In one embodiment, the first path may lie in a plane (e.g., the common plane).

The first path may define a motion curve (e.g., a trajectory that is formed by the first focus points). Therein, the first path may have an at least partially elliptical and/or eccentric course. In addition, the first path may have at least two (e.g., spatially and/or with regard to a recording time point of the first projection images) successive portions. Therein, each of the at least two portions of the first path may include at least one first focus point. Further, the at least two portions of the first path may include, at least partially (e.g., completely), different first focus points. The at least two portions of the first path may be considered, for example, as mutually adjacent angular regions. Therein, the angular regions may be defined by a first angle in the stationary center point. The limbs of the first angle are determined by the respectively first and last first focus point of the respective portion.

For the recording of the plurality of first projection images, the first isocenter may be repositioned, for example, relative to the stationary center point. The positioning of the first isocenter may include a translation of the movement direction of which is dependent upon the respective portion (e.g., the angular region of the first path). In other words, for recording the first projection images, the first focus points of which lie in a common portion (e.g., angular region) of the first path, the first isocenter may be repositioned substantially along a movement direction.

For example, for recording the first projection images, the first focus points of which lie in the first portion of the first path, the first isocenter may be repositioned substantially along a movement direction. In addition, for recording the first projection images, the first focus points of which lie in the second portion of the first path, the first isocenter may be repositioned substantially along a further movement direction. The further movement direction may be different from (e.g., oppositely directed to) the movement direction.

For example, the positioning of the first focus points and/or of the first isocenter may be parameterized dependent upon a further angle. The limbs of the further angle are determined by the respectively momentary first focus point and a reference straight line. In one embodiment, the reference straight line may extend through one of the first focus points and the stationary center point. Therein, the positioning of the first focus points and/or of the first isocenter may further have a periodicity with regard to the further angle. A period of the positioning of the first focus points may include at least two portions of the first path. Thereby, it may be provided that the first isocenter (e.g., the medical X-ray device) reaches the same spatial position and/or alignment after recording the first projection images as at the recording time point of the first projection image. Further, the parameterization of the positioning of the first focus points and/or of the first isocenter enables, dependent upon the respective portion of the first path (e.g., dependent upon the further angle), a particularly precise specification and/or control and/or adaptation of the recording geometry for recording the first projection images. In addition, the angular regions of the first path may be defined, in each case, by a value range of the further angle.

In a further embodiment of the method, first X-ray beams for forming the first projection images may each have a first aperture width in the first isocenter. Therein, the positioning of the first isocenter may take place, for example, along the movement direction within a first distance relative to the stationary center point. Further, as the first distance, not more than half the first aperture width may be specified.

The first X-ray beams may each have first edge rays, for example, limiting rays and a first central ray (e.g., a middle ray). Therein, the first edge rays may spatially delimit the first X-ray beam. In addition, the first central ray may extend through the first isocenter. The first aperture width may define a spatial distance along a first straight line that extends through the first isocenter and perpendicularly to the first central ray between the first edge rays.

Therein, the first aperture width may define a spatial distance between first edge rays of one of the first X-ray beams in each case. Thus, the first aperture width may characterize a spread of the first X-ray beam at the first isocenter. Additionally, the first aperture width may define an illumination width that characterizes, for example, together with an item of shape information regarding the first X-ray beam (e.g., a fan and/or a cone and/or a parallel form), a spatial region irradiatable by the first X-ray beam at the first isocenter.

Further, the first distance may define a spatial distance between the first isocenter and the stationary center point. In one embodiment, the positioning of the first isocenter may take place along the movement direction within the first distance relative to the stationary center point.

Through the specification of half the first aperture width as a maximum value for the first distance relative to the stationary center point, it may be provided that the stationary center point is irradiated in each of the first projection images by at least a part of the first X-ray beam emitted for recording. In other words, it may be provided thereby that the stationary center point is contained in each of the first projection images. This is advantageous, for example, for the reconstruction of the 3D image dataset from the first and second projection images.

In a further embodiment of the method, the second focus points may form a second path. Therein, the second path may have at least two successive portions that correspond, with regard to the stationary center point, to the at least two successive portions of the first path. In addition, the second projection images may be recorded about a second isocenter, which is repositioned for each recording. The positioning of the second isocenter may take place along a movement direction contrary to the movement direction for positioning the first isocenter in the corresponding portion of the first path relative to the stationary center point. In one embodiment, the second path may lie in a plane (e.g., in the common plane with the first path).

The second path may be a motion curve (e.g., a trajectory that is formed by the second focus points). Therein, the first path may have an at least partially elliptical and/or eccentric course. In addition, the second path may have at least two (e.g., spatially and/or with regard to a recording time point of the second projection images) successive portions that correspond to the at least two successive portions of the first path. For example, the second path may have exactly one portion corresponding to each of the at least two portions of the first path. Therein, each of the corresponding portions of the second path may include at least one second focus point. Further, the corresponding portions of the second path may include, at least partially (e.g., completely), different second focus points. The corresponding portions of the second path may be regarded, for example, as mutually adjacent angular regions. Therein, the angular regions may be defined by a second angle in the stationary center point. The limbs of the second angle are determined by the respectively first focus point and last second focus point of the respective corresponding portion. In one embodiment, a portion of the second path may have, respectively, a second focus point to at least one of the first focus points of the corresponding portion of the first path. Further, the angular regions of the second path may be defined by a value region of the further angle.

For the recording of the plurality of second projection images, the second isocenter may be repositioned, for example, relative to the stationary center point. Therein, the positioning of the second isocenter may include a translation, the movement direction of which is opposite (e.g., oppositely directed to the movement direction of the positioning of the first isocenter in the corresponding portion of the first path). For example, the first isocenter and the second isocenter may be contradirectionally positioned in corresponding portions of the first path and the second path.

Similarly to the positioning of the first focus points and/or of the first isocenter, the positioning of the second focus points and/or of the second isocenter may be parameterized dependent upon the further angle.

In one embodiment, the parameterization of the positioning of the second focus points and/or of the second isocenter enables, dependent upon the respective portion of the second path (e.g., dependent upon the further angle), a particularly precise specification and/or control and/or adaptation of the recording geometry for recording the second projection images.

By the parameterization of the first and second focus points, it may occur that first and second focus points of mutually corresponding first and second projection images have the same spatial position according to the parameterization. Provided that additionally the first projection direction and second projection direction of the mutually corresponding projection images match in these first and second focus points with the same spatial position, it may be advantageous to reduce an X-ray dose for recording the first projection image and/or second projection image in order to minimize a radiation burden for the examination object. In this case, in act (b), a corresponding second projection image of the examination object may be recorded for each of the first projection images.

Alternatively, at first focus points where, according to the parameterization, a second focus point with the same spatial position and the same second projection direction would be arranged, only one first projection image may be recorded in order to minimize the radiation burden for the examination object. In other words, the second projection image (e.g., the second focus point that, according to the parameterization, would be arranged at the same spatial position of the first focus point) may be omitted. In this case, in act (b), a corresponding second projection image of the examination object may be recorded only for a part of the first projection images.

In a further embodiment of the method, the positioning of the first isocenter and the second isocenter may take place at least in mutually corresponding portions of the first path and second path on a common straight line through the stationary center point.

The common straight line may extend through the first isocenter, the second isocenter, and the stationary center point (e.g., in a lateral direction). Further, the common straight line may be spatially stationary. In addition, the first focus points may each have a constant spatial distance (e.g., temporal) in relation to the first isocenter (e.g., at the time point of the recording of the respective first projection image). Further, the second focus points may each have a constant spatial distance (e.g., temporal) in relation to the second isocenter (e.g., at the time point of the recording of the respective second projection image). This is advantageous, for example, for the reconstruction of the 3D image dataset from the first and second projection images.

In a further embodiment of the method, second X-ray beams for generating the second projection images may each have a second aperture width in the second isocenter. The positioning of the second isocenter may take place within a second distance relative to the stationary center point. Further, as the second distance, not more than half the second aperture width may be specified.

The second X-ray beams may each have second edge rays (e.g., limiting rays and a second central ray, a middle ray). Therein, the second edge rays may spatially delimit the second X-ray beam. In addition, the second central ray may extend through the second isocenter. The second aperture width may define a spatial distance along a second straight line that extends through the second isocenter and perpendicularly to the second central ray between the second edge rays.

Therein, the second aperture width may define a spatial distance between first edge rays of one of the first X-ray beams in each case. Thus, the second aperture width may characterize a spread of the second X-ray beam at the second isocenter. Additionally, the second aperture width may define an illumination width that characterizes, for example, together with an item of shape information regarding the second X-ray beam (e.g., a fan and/or a cone and/or a parallel form), a spatial region irradiatable by the second X-ray beam at the second isocenter.

Further, the second distance may define a spatial distance between the second isocenter and the stationary center point. In one embodiment, the positioning of the second isocenter may take place within the second distance relative to the stationary center point.

Through the specification of half the second aperture width as a maximum value for the second distance relative to the stationary center point, it may be provided that the stationary center point is irradiated in each of the second projection images by at least a part of the second X-ray beam emitted for recording. In other words, it may be provided thereby that the stationary center point is contained in each of the second projection images. This is advantageous, for example, for the reconstruction of the 3D image dataset from the first and second projection images. Further, it may thereby be provided that each of the second projection images, together with the respective corresponding first projection image, at least partially maps a common part of the examination object about the stationary center point. In a borderline case, the common part may include a first edge ray and a second edge ray of the X-ray beam for recording the mutually corresponding projection images.

Further, the second X-ray beams may correspond with regard to the form and/or aperture width to the first X-ray beams. Therein, the first distance may be specified, for example, as the same as or different to the second distance.

In a further embodiment of the method, act c) may further include the acts c.1) to c.5). Therein, in act c.1), the first projection images may be extrapolated, for example, from the second projection images to an extended detector. Further, in act c.2), the second projection images may be extrapolated, for example, from the second projection images to an extended detector. In addition, in act c.3), a first 3D intermediate dataset may be generated by reconstruction of the extrapolated first projection images. In addition, in act c.4), a second 3D intermediate dataset may be generated by reconstructing the extrapolated second projection images. Thereafter, in act c.5), the first 3D intermediate dataset and the second 3D intermediate dataset may be averaged in a weighted manner to the 3D image dataset.

The extended detector may denote a virtual detector (e.g., a flat detector that has a larger surface for receiving the X-ray beams as compared with the real detector for recording the first and/or second projection images). Therein, for extrapolation of the first projection images onto the extended detector, missing detector values may be determined from the second projection images (e.g., by a resampling). Similarly thereto, for extrapolation of the second projection images onto the extended detector, missing detector values may be determined from the first projection images. The extrapolated first projection images may have a larger imaging region in relation to the examination object than the first projection images. Similarly thereto, the extrapolated second projection images may have a larger imaging region in relation to the examination object than the second projection images.

The first 3D intermediate dataset may be generated by reconstruction (e.g., analytical reconstruction) of the extrapolated first projection images. Further, the second 3D intermediate dataset may be generated by reconstruction (e.g., analytical reconstruction) of the extrapolated second projection images. Therein, the reconstruction of the first 3D intermediate dataset and/or second 3D intermediate dataset may include, for example, an inverse Radon transform of the respective extrapolated first and/or second projection images.

The 3D image dataset may map a volume of the examination object. Further, the 3D image dataset may have a plurality of image points (e.g., voxels). An image point in a plane of the recording geometry of the 3D image dataset is reconstructable (e.g., 3D reconstructable) if all line integrals that extend through the portion of the volume corresponding to the image point are mapped in the first and/or second projection images. Consequently, the 3D image dataset may have image points that are reconstructable purely from the first projection images or purely from the second projection images. Further, the 3D image dataset may have image points that are reconstructable both from the first and also the second projection images. In addition, the 3D image dataset may have image points that are reconstructable by the combination of the first and second projection images (e.g., mutually corresponding projection images). Therein, the image points may be classified with regard to reconstructability (e.g., by line tracing). Further, for reconstruction of the 3D image dataset, the weighted averaging of the first 3D intermediate dataset and second 3D intermediate dataset may take place in act c.5) based on the classification of the respective image point. For example, for the reconstruction of the image points that are reconstructable purely based on the first or second projection images, a corresponding image point of the associated 3D intermediate dataset may be used. Further, for the reconstruction of the image points that are reconstructable based on both of the first and the second projection images, a mean value of the associated image points of the first and second 3D intermediate datasets may be used. Similarly thereto, for the reconstruction of the image points that are reconstructable based on both the first and second projection images, a mean value of the associated image points of the first and second 3D intermediate datasets may be used.

By this, in the 3D image dataset, a volume of the examination object that has a larger spatial extent than a volume of the examination object reconstructable purely based on the first or second projection images may be mapped.

In a further embodiment of the method, act c.3) may include a filtered back projection of the extrapolated first projection images. Further, act c.4) may include a filtered back projection of the extrapolated second projection images.

Therein, the filtered back projection may include a Fourier transform of the extrapolated first and second projection images. Further, the filtered back projection may include a filtration (e.g., a high pass filtration and/or a low pass filtration and/or a windowing of the Fourier transform). Following an inverse transform of the filtered Fourier transforms, the 3D intermediate datasets may be reconstructed respectively by a back projection of the filtered inverse transform.

By this, a particularly computation-efficient reconstruction of the 3D intermediate datasets may be enabled.

The present embodiments relate, in a second aspect, to a medical X-ray device including, for example, a provision unit that is configured for carrying out a proposed method for providing a 3D image dataset of an examination object. The medical X-ray device (e.g., the provision unit) may be configured for carrying out the method in that the components of the medical X-ray device (e.g., components of the provision unit) are configured for carrying out the individual acts of the method. For example, the medical X-ray device may be configured for recording and/or for providing the first and second projection images of the examination object.

The advantages of the medical X-ray device of the present embodiments substantially correspond to the advantages of the method for providing a 3D image dataset of an examination object of the present embodiments. Features, advantages, or alternative embodiments mentioned herein may also be transferred to the other subject matter and vice versa.

In a third aspect, the present embodiments relate to a computer program product with a computer program that may be directly loaded into a memory store of a provision unit, having program portions in order to carry out all the acts of the method for providing a 3D image dataset of an examination object when the program portions are executed by the provision unit. The computer program product may therein include an item of software with a source code that still have to be compiled and linked or only have to be interpreted, or an executable software code that, for execution, only have to be loaded into the provision unit. Using the computer program product, the method for providing a 3D image dataset of an examination object by a provision unit may be carried out in a rapid, exactly reproducible and robust manner. The computer program product is configured such that the computer program product may carry out the method acts according to the present embodiments by the provision unit.

The computer program product is stored, for example, on a computer-readable storage medium or is deposited on a network or server from where the computer program product may be loaded into the processor of a provision unit that may be directly connected to the provision unit, or may be configured as part of the provision unit. Further, control information of the computer program product may be stored on an electronically readable data carrier. The items of control information of the electronically readable data carrier may be configured such that the items of control information carry out a method according to the present embodiments when the data carrier is used in a provision unit. Examples of electronically readable data carriers are a DVD, a magnetic tape, or a USB stick, on which electronically readable control information (e.g., software) is stored. If these items of control information are read from the data carrier and stored in a provision unit, all the embodiments of the above-described methods may be carried out.

The present embodiments may also relate to a computer-readable storage medium and/or an electronically readable data carrier on which program portions that may be read and executed by a provision unit are stored in order to carry out all the acts of the method for providing a 3D image dataset of an examination object when the program portions are executed by the provision unit.

A realization largely through software has the advantage that conventionally used provision units may also easily be upgraded with a software update in order to operate in the manner according to the present embodiments. Such a computer program product may include, where relevant, in addition to the computer program, additional constituents, such as, for example, documentation and/or additional components as well as hardware components (e.g., hardware keys (dongles, etc.) in order to use the software).

BRIEF DESCRIPTION OF THE DRAWINGS

Exemplary embodiments are illustrated in the drawings and are described in greater detail below. In the different figures, the same reference signs are used for the same features. In the drawings.

DETAILED DESCRIPTION

Figure 1:
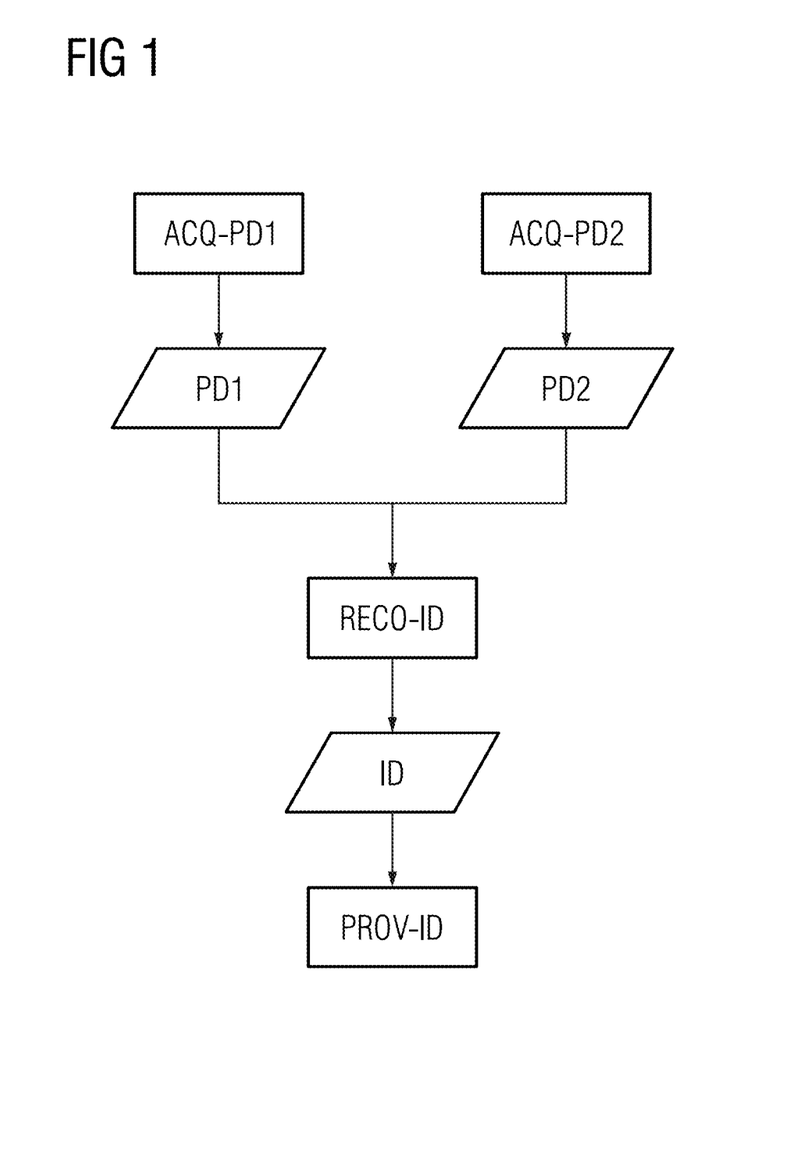
FIG. 1 shows a schematic representation of one embodiment of a method.

FIG. 1 shows schematically an embodiment of a method for providing a three-dimensional (3D) image dataset of an examination object. Therein, in a first act a), a plurality of first projection images PD1 of the examination object may be recorded ACQ-PD1. Therein, the plurality of first projection images PD1 may map the examination object along mutually different first projection directions. In a second act (b), a corresponding second projection image PD2 of the examination object in each case may be recorded ACQ-PD2 for at least two of the first projection images PD1. Therein, the first projection images PD1 may each have a first focus point, and the second projection images PD2 may each have a second focus point. In addition, each of the second projection images PD2 together with the respective first projection images PD1 corresponding thereto may at least partially map a common part of the examination object about a stationary center point. Further, the second projection images PD2 may map the examination object along second projection directions that are mutually different and at least partially different, relative to the first projection direction of the respectively corresponding first projection image PD1, such that a straight line through the first and the second focus point of the mutually corresponding first PD1 and second PD2 projection images extends through the stationary center point. In a third act c), the 3D image dataset ID may be reconstructed RECO-ID from the first PD1 and second projection images PD2. Thereafter, in a fourth act d), the 3D image dataset ID may be provided PROV-ID.

Figure 2:
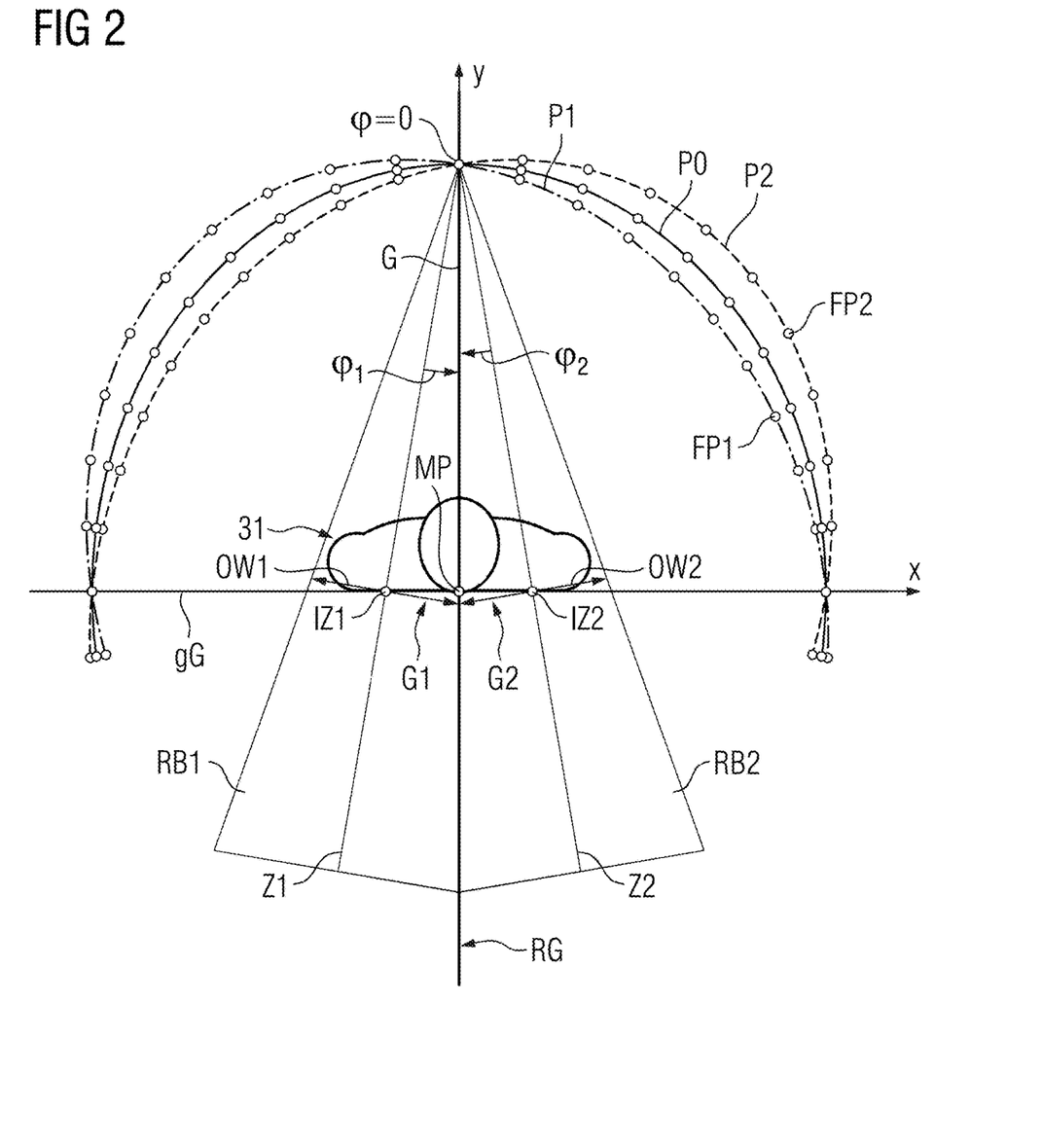
FIGS. 2 and 3 show schematic representations of different recording geometries for recording a plurality of first and second projection images according to an embodiment of the method.
Figure 3:
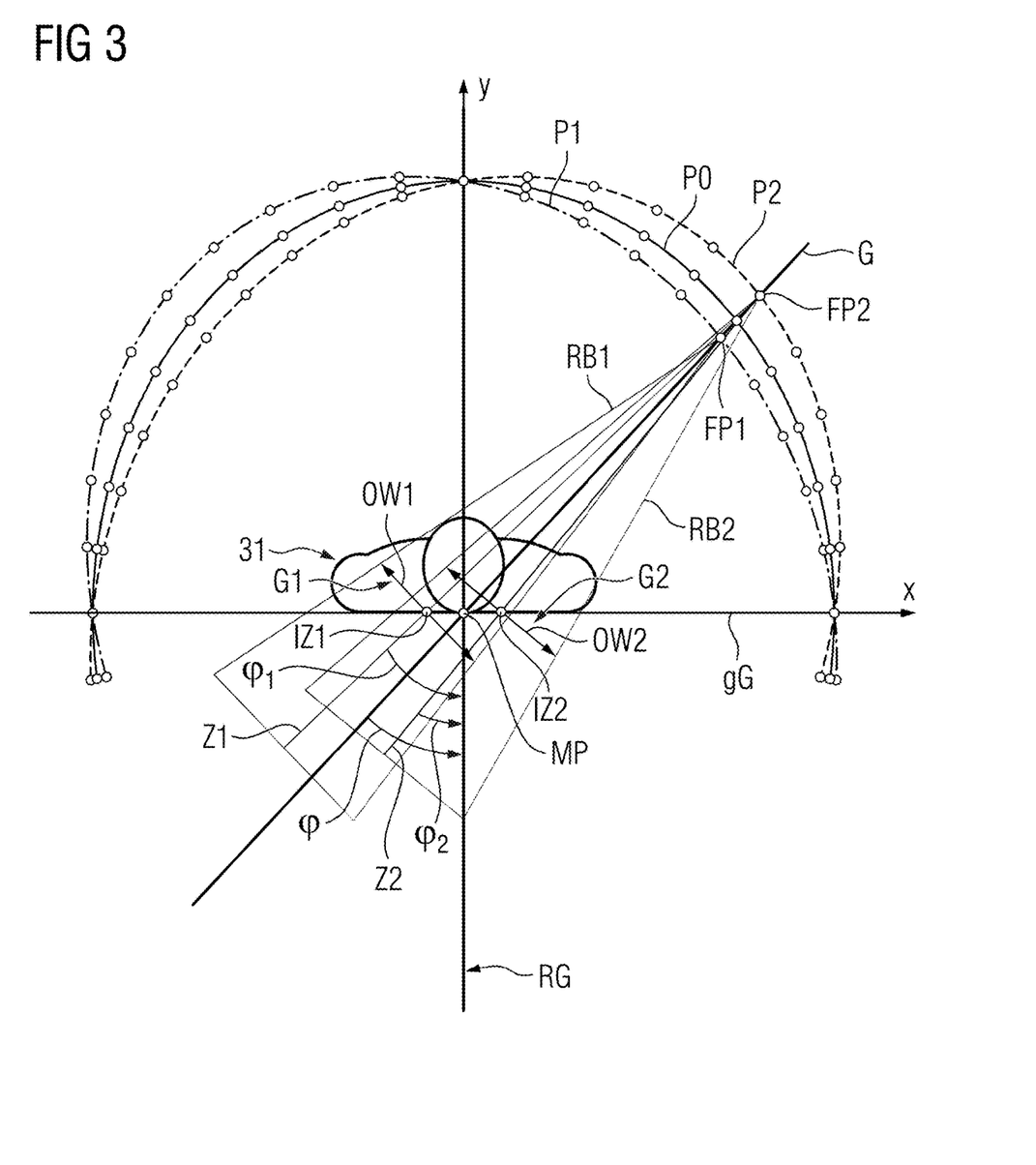

FIGS. 2 and 3 show schematic representations of different recording geometries for recording the first PD1 and second projection images PD2. Therein, the first focus points FP1 may form a first path P1. Similarly thereto, the second focus points FP2 may form a second path P2.

Further, the first focus points FP1 may each define a spatial position of the meeting of X-rays of a first X-ray beam RB1 at the time point of the recording of the respective first projection image PD1. Similarly thereto, the second focus points FP2 may have a spatial position of the meeting of the X-rays of a second X-ray beam RB2 at the time point of the recording of the respective second projection image PD2. In addition, the first focus point FP1 and/or the second focus point FP2 may each define a spatial position of an X-ray source at the time point of the recording of the respective projection image.

In one embodiment, the straight line G may extend through the first focus point FP1 and the second focus point FP2 of respectively mutually corresponding first PD1 and second projection images PD2 through the stationary center point MP. Further, the first projection images PD1 may be recorded about a first isocenter IZ1 that may be repositioned for each recording. Therein, a spatial distance between the first focus points FP1 and the first isocenter IZ1 may be constant at the respective time point of the recording of the associated first projection image PD1. Similarly thereto, the second projection images PD2 may be recorded about a second isocenter IZ2 that may be repositioned for each recording. Therein, a spatial distance between the second focus points FP2 and the second isocenter IZ2 may be constant, in each case, at the time point of the recording of the associated second projection image PD2. For example, the spatial distance between the second focus points FP2 and the second isocenter IZ2, in each case, at the time point of the recording of the associated second projection image PD2 may be equal to the spatial distance between the first focus points FP1 and the first isocenter IZ1 at the time point, in each case, of the recording of the associated first projection image PD1.

Further, the first path P1 may have at least two successive portions. In one embodiment, the first path P1 may have a course deviating at least partially from a circular path P0 (e.g., an elliptical and/or eccentric course). The at least two portions of the first path P1 may be considered, for example, as mutually adjacent angular regions. Therein, the angular regions may be defined by a first angle (not shown here) in the stationary center point MP. Limbs of the first angle are determined by the respective first and last first focus point FP1 of the respective portion. In the exemplary embodiment illustrated in FIGS. 2 and 3, the successive portions (e.g., the angular regions) may be formed by portions of the first path P1 in paired successive quadrants of the coordinate system shown (e.g., in successive value ranges of the further angle that may each include 180°).

In addition, the positioning of the first isocenter IZ1 may take place along a movement direction relative to the stationary center point MP. The movement direction is dependent upon the respective portion of the first path P1. Further, the second path P2 may have at least two successive portions that correspond, with regard to the stationary center point MP, to the at least two successive portions of the first path. Therein, the second path P2 may have a course deviating at least partially from the circular path P0 (e.g., an elliptical and/or eccentric course). The at least two portions of the second path P2 may be considered (e.g., as adjacent angular regions). Therein, the angular regions may be defined by a second angle (not shown here) in the stationary center point MP. Limbs of the second angle are determined by the respective first and last first focus point FP2 of the respective portion. In the exemplary embodiment illustrated in FIGS. 2 and 3, the successive portions (e.g., the angular regions) may be formed by portions of the second path P2 in paired successive quadrants of the coordinate system shown, for example, in successive value ranges of the further angle that may each include, for example, 180°. In one embodiment, the respective mutually corresponding portions of the first path P1 and of the second path P2 have the same angular region with regard to the stationary center point MP. Therein, the positioning of the second isocenter IZ2 may take place along a movement direction opposite to the movement direction for positioning the first isocenter IZ1 in the corresponding portion of the first path P1 relative to the stationary center point MP.

For example, the positioning of the first isocenter IZ1 and the second isocenter IZ2 may take place at least in mutually corresponding portions of the first P1 and the second path P2 on a common straight line gG. The common straight line gG extends through the stationary center point MP.

The first X-ray beams RB1 may each have first edge rays and a first central ray Z1 (e.g., a middle ray). Therein, the first central ray Z1 may extend through the first isocenter IZ1. Further, the first X-ray beams RB1 may each have a first aperture width OW1 in the first isocenter IZ1. The first aperture width OW1 defines a spatial distance along a first straight line G1 between the first edge rays. The first straight line G1 extends through the first isocenter IZ1 and perpendicularly to the first central ray Z1. The positioning of the first isocenter IZ1 may take place along the common straight line gG (e.g., within a first distance in relation to the stationary center point MP). As the first distance, not more than half the first aperture width OW1 is specified. Similarly thereto, the second X-ray beams RB2 may each have second edge rays and a second central ray Z2 (e.g., a middle ray). Therein, the second central ray Z2 may extend through the second isocenter IZ2. Further, the second X-ray beams RB2 may each have a second aperture width OW2 in the second isocenter IZ2. The aperture width defines a spatial distance along a second straight line G2 between the second edge rays. The second straight line G2 extends through the second isocenter IZ2 and perpendicularly to the first central ray Z2. Further, the positioning of the second isocenter IZ2 may take place along the common straight line gG within a second distance in relation to the stationary center point MP. As the second distance, not more than half the second aperture width OW2 is specified. The first X-ray beam RB1 and/or the second X-ray beam RB2 may have the form of a conical beam and/or a fan beam and/or a parallel beam (not shown here).

For example, the positioning of the first focus points FP1 and/or of the first isocenter IZ1 may be parameterized dependent upon a further angle $\varphi$ (e.g., in the stationary center point MP). Limbs of the further angle $\varphi$ are determined by the respectively momentary first focus point FP1 and a reference straight line RG. Similarly thereto, the positioning of the second focus points FP2 and/or of the second isocenter IZ2 may be parameterized dependent upon the further angle $\varphi$.

If, for example, a number of n first projection images PD1 is recorded at n first focus points FP1, a number of n second projection images PD2 corresponding thereto may also be recorded at n second focus points FP2. In one embodiment, the first focus pint FP1 and the second focus point FP2 may have a constant spatial distance r in relation to the respective isocenter. Therein, a spatial position of the first focus point FP1 and the second focus point FP2 may be parameterized by the further angle $$\varphi = \varphi(n) \tag{1}$$

The further angle $\varphi$ may therein define, for example, a projection angle of a projection mapping resulting from the first PD1 and second projection images PD2 corresponding to one another.

Therein, the spatial position of the first isocenter IZ1 may be specified by:

$$\vec{x_1}(n) = \begin{pmatrix} -d_1 \cdot \cos(\varphi(n)) \\ 0 \end{pmatrix} \tag{2}$$

where $d_1$ denotes the first distance. Similarly, the spatial position of the second isocenter IZ2 may be specified by:

$$\vec{x_2}(n) = \begin{pmatrix} d_2 \cdot \cos(\varphi(n)) \\ 0 \end{pmatrix} \tag{3}$$

such that a movement direction of the positioning of the second isocenter IZ2 is oppositely directed to the movement direction of the positioning of the first isocenter IZ1, where $d_2$ denotes the second distance.

In addition, the first focus points FP1 (e.g., the first central ray Z1 in the first isocenter IZ1) each have a first orbital angle $\varphi_1$ relative to the reference straight line RG. Similarly thereto, the second focus points FP2 (e.g., the second central ray Z2 in the second isocenter IZ2) each have a second orbital angle $\varphi_2$ relative to the reference straight line RG.

According to equation (2), the first orbital angle is defined by:

$$\varphi_1(n) = \varphi(n) + \arcsin\left(\frac{d_1}{r} \cdot \cos^2(\varphi(n))\right) \tag{4}$$

Further, according to equation (3), the second orbital angle is defined by:

$$\varphi_2(n) = \varphi(n) - \arcsin\left(\frac{d_2}{r} \cdot \cos^2(\varphi(n))\right) \tag{5}$$

In one embodiment, by this, the positioning of the first focus point FP1 and the second focus point FP2 and/or of the first isocenter IZ1 and of the second isocenter IZ2 may have a periodicity in relation to the further angle cp. In addition, the first distance $d_1$ may be equal to the second distance $d_2$:

$$d_1 = d_2 \tag{6}$$

Figure 4:
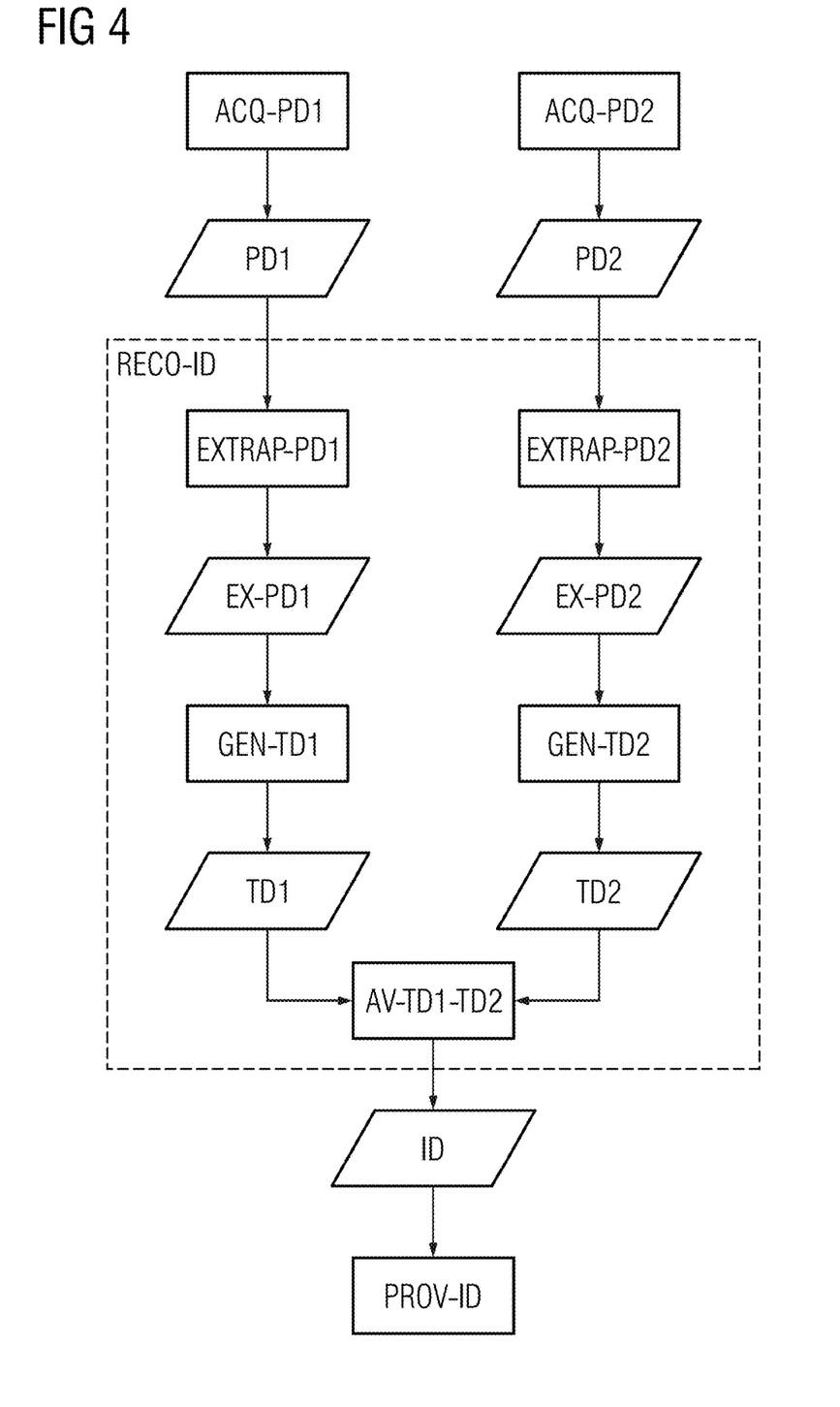
FIG. 4 shows a schematic representation of a further embodiment of the method.

FIG. 4 shows schematically a further embodiment of the method. Therein, act c) may include further subacts. In a first subact c.1), the first projection images PD1 may be extrapolated EXTRAP-PD1 to an extended detector. Further, in a second subact c.2), the second projection images PD2 may be extrapolated EXTRAP-PD2 to the extended detector. In a further subact c.3), a first 3D intermediate dataset TD1 may be generated GEN-TD1 by reconstruction of the extrapolated first projection images EX-PD1. Further, in a subact c.4), a second 3D intermediate dataset TD2 may be generated GEN-TD2 by reconstruction of the extrapolated second projection images EX-PD2. Thereafter, the first TD1 and the second 3D intermediate dataset TD2 may be averaged AV-TD1-TD2 in a weighted manner to the 3D image dataset ID.

In one embodiment, acts c.3) and c.4) may include a filtered back projection of the respectively extrapolated first EX-PD1 and second projection images EX-PD2.

Figure 5:
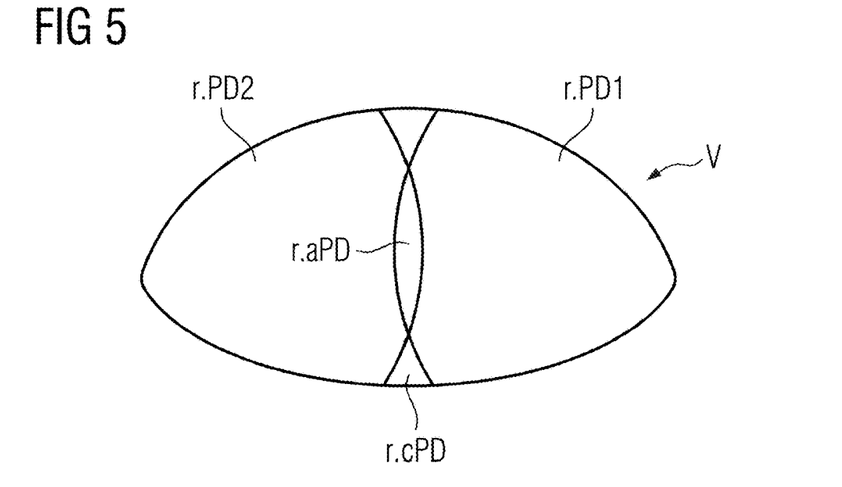
FIG. 5 shows a schematic representation of different portions of a reconstructable volume.

FIG. 5 shows a schematic representation of different portions of the volume V of the examination object 31 that is reconstructable to the 3D image dataset ID. The 3D image dataset ID may have a plurality of image points (e.g., voxels). An image point in a plane of the recording geometry of the 3D image dataset ID is reconstructable (e.g., three-dimensionally reconstructable) if all line integrals that extend through the portion of the volume V corresponding to the image point are mapped in the first projection images PD1 and/or second projection images PD2.

The image points of the 3D image dataset may be classified with regard to reconstructability, for example, using line tracing. In FIG. 5, the different spatial portions of the volume V reconstructed to the 3D image dataset ID are classified dependent upon the respective reconstructability. The 3D image dataset ID may have image points r.PD1 that are reconstructable purely from the first projection images PD1. Similarly, the 3D image dataset ID may have image points r.PD2 that are reconstructable purely from the second projection images PD2. Further, the 3D image dataset ID may have image points r.aPD that are reconstructable both from the first projection images PD1 and also the second projection images PD2. In addition, the 3D image dataset ID may have image points r.cPD that are reconstructable by the combination of the first projection images PD1 and the second projection images PD2 (e.g., mutually corresponding). In one embodiment, for the reconstruction of the 3D image dataset ID, a weighted averaging of the first 3D intermediate dataset TD1 and the second 3D intermediate dataset TD2 may take place in act c.5) based on the classification of the respective image point (r.PD1, r.PD2, r.aPD, r.cPD).

Figure 6:
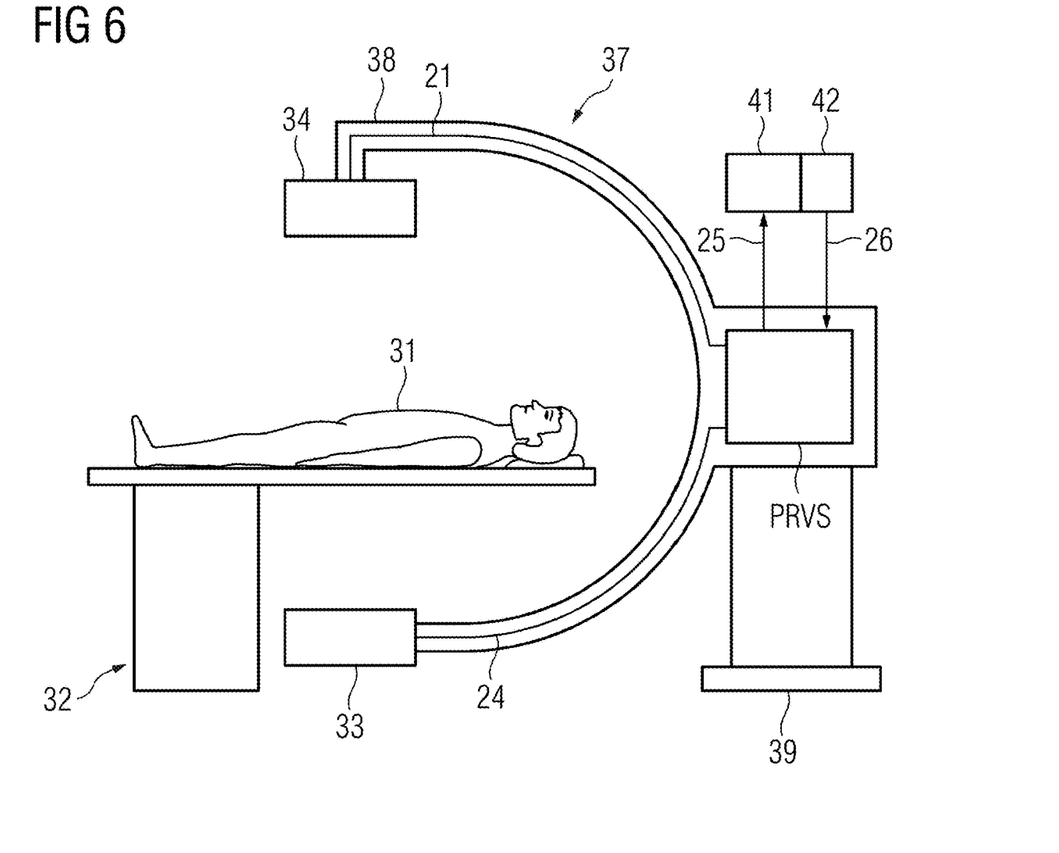
FIG. 6 shows a schematic representation of one embodiment of a medical X-ray device.

FIG. 6 shows a schematic representation of a medical C-arm X-ray device 37 as an example of a proposed medical X-ray device. Therein, the medical C-arm X-ray device 37 may include a provision unit PRVS. Therein, the medical C-arm X-ray device 37 (e.g., the provision unit PRVS) may be configured for carrying out a proposed method for providing PROV-ID a 3D image dataset of an examination object 31.

Herein, the medical C-arm X-ray device 37 also includes a detector 34 (e.g., an X-ray detector) and an X-ray source 33. For recording the first projection images PD1 and the second projection images PD2, an arm 38 of the C-arm X-ray device 37 may be mounted such that the arm 38 may move about one or more axes. Further, the medical C-arm X-ray device 37 may include a movement apparatus 39 that enables a movement of the C-arm X-ray device 37 in the space.

For recording the first projection images PD1 and the second projection images PD2 of the examination object 31 arranged on a patient positioning apparatus 32, the provision unit PRVS may transmit a signal 24 to the X-ray source 33. Thereupon, the X-ray source 33 may emit an X-ray beam (e.g., the first X-ray beam RB1 and/or the second X-ray beam RB2). When the respective X-ray beam RB1 and/or RB2 impinges upon a surface of the detector unit 34 following an interaction with the examination object 31, the detector unit 34 may emit a signal 21 to the provision unit PRVS. The provision unit PRVS may receive the first projection image PD1 and the second projection image PD2, for example, based on the signal 21.

In addition, the medical C-arm X-ray device 37 may include an input unit 42 (e.g., a keyboard) and/or a display unit 41 (e.g., a monitor and/or display). The input unit 42 may be integrated into the display unit 41, for example, in the case of a capacitive input display. Therein, by an input by the operating person on the input unit 42, a control of the medical C-arm X-ray device 37 (e.g., the method for providing PROV-ID), a 3D image dataset ID of an examination object 31 may be enabled. For this purpose, the input unit 42 may transmit, for example, a signal 26 to the provision unit PRVS.

Further, the display unit 41 may be configured to display information and/or graphical representations of information of the medical C-arm X-ray device 37 and/or of the provision unit PRVS and/or further components. For this purpose, the provision unit PRVS may transmit, for example, a signal 25 to the display unit 41. For example, the display unit 41 may be configured for the display of a graphical representation of the first projection images PD1 and/or second projection images PD2 and/or of the 3D image dataset ID and/or of the first 3D intermediate dataset TD1 and/or the second 3D intermediate dataset TD2.

The schematic representations contained in the drawings described do not show any scale or size relation.

The methods described above in detail and the apparatuses disclosed are merely exemplary embodiments that may be modified by a person skilled in the art in a wide variety of ways without departing from the scope of the invention. Further, the use of the indefinite article "a" or "an" does not preclude the possibility that the relevant features may also be present plurally. Similarly, the expressions "unit" and "element" do not preclude the components in question consisting of a plurality of cooperating subcomponents that may also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for providing a three-dimensional (3D) image dataset of an examination object, the method comprising:
   recording a plurality of first projection images of the examination object, wherein the plurality of first projection images map the examination object along mutually different first projection directions;
   recording a corresponding respective second projection image of the examination object for at least two first projection images of the plurality of first projection images, wherein each first projection image of the plurality of first projection images has a first focus point, and the second projection images each have a second focus point, wherein each of the second projection images together with the respective first projection images corresponding thereto at least partially map a common part of the examination object about a stationary center point, wherein the second projection images map the examination object along second projection directions that are mutually different and, in relation to the respective corresponding first projection directions, at least partially different, such that a straight line through the first focus point and the second focus point of the mutually corresponding first projection images and second projection images extends through the stationary center point;

reconstructing the 3D image dataset from the plurality of first projection images and the second projection images; and providing the 3D image dataset.

2. The method of claim 1, wherein the first focus points form a first path, wherein the first path has at least two successive portions, wherein the plurality of first projection images are recorded about a first isocenter that is repositioned for each recording, and wherein positioning of the first isocenter along a movement direction takes place relative to the stationary center point, the movement direction being dependent upon a respective portion of the first path.

3. The method of claim 2, wherein first X-ray beams for generating the plurality of first projection images each have a first aperture width in the first isocenter, wherein the positioning of the first isocenter takes place within a first distance relative to the stationary center point, and wherein, as the first distance, not more than half the first aperture width is specified.

4. The method of claim 2, wherein the second focus points form a second path, wherein the second path has at least two successive portions that correspond, with regard to the stationary center point, to the at least two successive portions of the first path, wherein the second projection images are recorded about a second isocenter, the second isocenter being repositioned for each recording, wherein the positioning of the second isocenter takes place along a movement direction contrary to the movement direction for positioning the first isocenter in the corresponding portion of the first path relative to the stationary center point.

5. The method of claim 4, wherein the positioning of the first isocenter and the second isocenter takes place at least in mutually corresponding portions of the first path and the second path on a common straight line through the stationary center point.

6. The method of claim 4, wherein second X-ray beams for generating the second projection images each have a second aperture width in the second isocenter, wherein the positioning of the second isocenter takes place within a second distance relative to the stationary center point, and wherein, as the second distance, not more than half the second aperture width is specified.

7. The method of claim 1, wherein reconstructing the 3D image dataset further comprises:

extrapolating the plurality of first projection images to an extended detector;

extrapolating the second projection images to the extended detector;

generating a first 3D intermediate dataset, the generating of the first 3D intermediate dataset comprising reconstructing the plurality of extrapolated first projection images;

generating a second 3D intermediate dataset, the generating of the second 3D intermediate dataset comprising reconstructing the extrapolated second projection images; and weighted averaging the first 3D intermediate dataset and the second 3D intermediate dataset to the 3D image dataset.

8. The method of claim 7, wherein generating the first 3D intermediate dataset comprises filtered back projecting the plurality of extrapolated first projection images, and wherein generating the second 3D intermediate dataset comprises filtered back projecting the extrapolated second projection images.

9. A medical X-ray device comprising:

a processor configured to:

record a plurality of first projection images of the examination object, wherein the plurality of first projection images map the examination object along mutually different first projection directions;

record a corresponding respective second projection image of the examination object for at least two first projection images of the plurality of first projection images, wherein each first projection image of the plurality of first projection images has a first focus point, and the second projection images each have a second focus point, wherein each of the second projection images together with the respective first projection images corresponding thereto at least partially map a common part of the examination object about a stationary center point, wherein the second projection images map the examination object along second projection directions that are mutually different and, in relation to the respective corresponding first projection directions, at least partially different, such that a straight line through the first focus point and the second focus point of the mutually corresponding first projection images and second projection images extends through the stationary center point;

reconstruct the 3D image dataset from the plurality of first projection images and the second projection images; and provide the 3D image dataset.

10. In a non-transitory computer-readable storage medium that stores instructions executable by one or more processors to provide a three-dimensional (3D) image dataset of an examination object, the instructions comprising:

recording a plurality of first projection images of the examination object, wherein the plurality of first projection images map the examination object along mutually different first projection directions;

recording a corresponding respective second projection image of the examination object for at least two first projection images of the plurality of first projection images, wherein each first projection image of the plurality of first projection images has a first focus point, and the second projection images each have a second focus point, wherein each of the second projection images together with the respective first projection images corresponding thereto at least partially map a common part of the examination object about a stationary center point, wherein the second projection images map the examination object along second projection directions that are mutually different and, in relation to the respective corresponding first projection directions, at least partially different, such that a straight line through the first focus point and the second focus point of the mutually corresponding first projection images and second projection images extends through the stationary center point;

reconstructing the 3D image dataset from the plurality of first projection images and the second projection images; and providing the 3D image dataset.

11. The non-transitory computer-readable storage medium of claim 10, wherein the first focus points form a first path, wherein the first path has at least two successive portions, wherein the plurality of first projection images are recorded about a first isocenter that is repositioned for each recording, and wherein positioning of the first isocenter along a movement direction takes place relative to the stationary center point, the movement direction being dependent upon a respective portion of the first path.

12. The non-transitory computer-readable storage medium of claim 11, wherein first X-ray beams for generating the plurality of first projection images each have a first aperture width in the first isocenter, wherein the positioning of the first isocenter takes place within a first distance relative to the stationary center point, and wherein, as the first distance, not more than half the first aperture width is specified.

13. The non-transitory computer-readable storage medium of claim 11, wherein the second focus points form a second path, wherein the second path has at least two successive portions that correspond, with regard to the stationary center point, to the at least two successive portions of the first path, wherein the second projection images are recorded about a second isocenter, the second isocenter being repositioned for each recording, and wherein the positioning of the second isocenter takes place along a movement direction contrary to the movement direction for positioning the first isocenter in the corresponding portion of the first path relative to the stationary center point.

14. The non-transitory computer-readable storage medium of claim 13, wherein the positioning of the first isocenter and the second isocenter takes place at least in mutually corresponding portions of the first path and the second path on a common straight line through the stationary center point.

15. The non-transitory computer-readable storage medium of claim 13, wherein second X-ray beams for generating the second projection images each have a second aperture width in the second isocenter, wherein the positioning of the second isocenter takes place within a second distance relative to the stationary center point, and wherein, as the second distance, not more than half the second aperture width is specified.

16. The non-transitory computer-readable storage medium of claim 10, wherein reconstructing the 3D image dataset further comprises:

extrapolating the plurality of first projection images to an extended detector;

extrapolating the second projection images to the extended detector;

generating a first 3D intermediate dataset, the generating of the first 3D intermediate dataset comprising reconstructing the plurality of extrapolated first projection images;

generating a second 3D intermediate dataset, the generating of the second 3D intermediate dataset comprising reconstructing the extrapolated second projection images; and weighted averaging the first 3D intermediate dataset and the second 3D intermediate dataset to the 3D image dataset.

17. The non-transitory computer-readable storage medium of claim 16, wherein generating the first 3D intermediate dataset comprises filtered back projecting the plurality of extrapolated first projection images, and wherein generating the second 3D intermediate dataset comprises filtered back projecting the extrapolated second projection images.

* * * * *